United States Patent
Staehle et al.

(10) Patent No.: US 9,416,133 B2
(45) Date of Patent: Aug. 16, 2016

(54) HYDROPYRROLOPYRROLE DERIVATIVES FOR USE AS FATTY ACID SYNTHASE INHIBITORS

(71) Applicant: MERCK PATENT GMBH, Darmstadt (DE)

(72) Inventors: Wolfgang Staehle, Ingelheim (DE); Christos Tsaklakidis, Weinheim (DE); Birgitta Leuthner, Darmstadt (DE); Dirk Wienke, Darmstadt (DE); Frank Czauderna, West Roxbury, MA (US); Ansgar Wegener, Heusenstamm (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 14/430,630

(22) PCT Filed: Aug. 30, 2013

(86) PCT No.: PCT/EP2013/002606
§ 371 (c)(1),
(2) Date: Mar. 24, 2015

(87) PCT Pub. No.: WO2014/044356
PCT Pub. Date: Mar. 27, 2014

(65) Prior Publication Data
US 2015/0252046 A1    Sep. 10, 2015

(30) Foreign Application Priority Data

Sep. 24, 2012 (EP) .................................. 12006668

(51) Int. Cl.
*C07D 487/04* (2006.01)
*A61K 31/407* (2006.01)
*A61K 31/4725* (2006.01)

(52) U.S. Cl.
CPC ............ *C07D 487/04* (2013.01); *A61K 31/407* (2013.01); *A61K 31/4725* (2013.01)

(58) Field of Classification Search
None
See application file for complete search history.

(56) References Cited

U.S. PATENT DOCUMENTS

| 8,614,238 | B2 | 12/2013 | Kley et al. |
| 2007/0191335 | A1 | 8/2007 | Lemoine et al. |
| 2012/0208827 | A1 | 8/2012 | Dock et al. |
| 2013/0053412 | A1 | 2/2013 | Kley et al. |
| 2013/0237535 | A1 | 9/2013 | Adams et al. |

FOREIGN PATENT DOCUMENTS

| WO | 2011048018 A1 | 4/2011 |
| WO | 2012064642 A1 | 5/2012 |
| WO | 2013028445 A1 | 2/2013 |

OTHER PUBLICATIONS

International Search Report for PCT/EP2013/002606 dated Oct. 2, 2013.

*Primary Examiner* — Zinna Northington Davis
(74) *Attorney, Agent, or Firm* — Millen, White, Zelano, Branigan, P.C.

(57) ABSTRACT

Compounds of the formula I
in which $R^1$, $R^2$, R, $X^1$, $X^2$, $X^3$, $X^4$, n1, n2, n3 and n4 have the meanings indicated in claim 1,
are inhibitors of Tankyrase, and can be employed, inter alia, for the treatment of diseases such as cancer, cardiovascular diseases, central nervous system injury and different forms of inflammation.

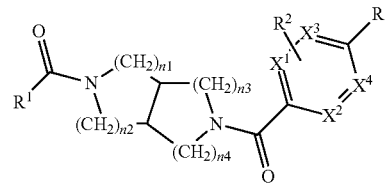

20 Claims, No Drawings

HYDROPYRROLOPYRROLE DERIVATIVES FOR USE AS FATTY ACID SYNTHASE INHIBITORS

TECHNICAL FIELD OF THE INVENTION

The present invention relates to novel hydropyrrolopyrrole derivatives which inhibit the activity of fatty acid synthase (FASN; also abbreviated as FAS), to pharmaceutical compositions comprising them, to processes for their preparation, and to their use in therapy for the treatment of cancers.

BACKGROUND OF THE INVENTION

Fatty Acid Synthase (FAS) is a critical enzyme for endogenous lipogenesis and plays an important role in the modulation of key intermediates of lipid and carbohydrate cellular metabolism. FAS is highly expressed in the tissues with high metabolic activity (for example liver, adipose tissue and brain) and there are good reasons to believe that a FAS inhibitor would cause beneficial metabolic effects in peripheral tissues. In addition, inhibition of FAS in the hypothalamus may result in reduced food intake. The non-specific irreversible FAS inhibitors cerulenin and C-75 have been reported in the literature to decrease brain levels of orexigenic neuropeptides and to decrease food intake.

FAS is also highly expressed in human sebocytes, the lipid producing cells of the sebaceous glands. Acne is the most common disorder involving the sebaceous gland. The pathogenesis of acne involves lipid (over)production by the sebaceous gland and it has been reported that inhibitors of mammalian FAS inhibit the production of sebum in sebocytes (US 2005/0053631). Acne cannot occur without sebum lipids. There is an unmet medical need in the treatment of acne for agents that reduce sebum production.

Since fatty acid synthesis in bacteria is essential for cell survival, bacterial FAS (type II synthase) has emerged as a potential target for antibacterial therapy. Unlike in most other prokaryotes, fatty acid synthase activity in mycobacteria is carried out by a single high-molecular-weight, multifunctional peptide chain (type I synthase) related to mammalian FAS. Mycobacterial type I FAS has been described as a potential target for antimycobacterial therapy, e.g. the treatment of *tuberculosis*. With one-third of the world's population being infected with the *tuberculosis bacillus*, and multidrug-resistant strains of *Mycobacterium tuberculosis* developing, there is a high medical need for novel *tuberculosis* therapies. (Silvana C. Ngo, et al.: Inhibition of isolated *Mycobacterium tuberculosis* Fatty Acid Synthase I by Pyrazinamide Analogs; Antimicrobial agents and Chemotherapy 51,7 (2007) 2430-2435).

Recently, microdomains of organelle membranes rich in sphingomyelin and cholesterol (called "lipid rafts") have been considered to act as a scaffold for the hepatitis C virus (HCV) replication complex (F. Amemiya, et al.: Targeting Lipid Metabolism in the Treatment of Hepatitis C Virus Infection. The Journal of Infectious Diseases 197 (2008) 361-70). Consequently, alterations of membrane lipid composition and/or distribution may influence viral replication. Indeed, agents related to lipid metabolism like polyunsaturated fatty acids or HMG-CoA reductase inhibitors (statins) have been shown to affect the replication of genotype 1 HCV (dto). These agents may attenuate HCV replication through the destruction of lipid rafts, according to their pharmacological actions. An alternative molecular mechanism possibly responsible for the inhibition of HCV replication is via altering localization of host proteins through alterations in lipid anchoring (S. M. Sagan, et al.: The influence of cholesterol and lipid metabolism on host cell structure and hepatitis C virus replication. Biochem. Cell Biol. 84 (2006) 67-79). Unlike polyunsaturated fatty acids, addition of saturated fatty acids or oleic acid to cultured Sfil cells promoted HCV RNA replication (S. B. Kapadia, F. V. Chisari: Hepatitis C virus RNA replication is regulated by host geranylgeranylation and fatty acids. PNAS 102 (2005) 2561-66). In line with this, it has been reported that expression of fatty acid synthase was increased in a human hepatoma cell line upon HCV infection (W. Yang, et al.: Fatty acid synthase is up-regulated during hepatitis C virus infection and regulates hepatitis C virus entry. Hepatology 48,5 (2008) 1396-1403). Furthermore, inhibition of fatty acid biosynthesis by TOFA (an inhibitor of acetyl-CoA carboxylase) or inhibitors of fatty acid synthase (cerulenin, C75), led to decreased HCV production (dto).

The effect of fatty acid synthase (FAS) activity on viral replication or infection appears not to be restricted to HCV, but has also been reported for HIV (D. H. Nguyen, D. D. Taub: Targeting Lipids to Prevent HIV infection. Molecular Interventions 4,6 (2004) 318-320), Poliovirus (R. Guinea, L. Carrasco: Effects of Fatty Acids on Lipid Synthesis and Viral RNA Replication in Poliovirus-Infected Cells. Virology 185 (1991) 473-476), Epstein-Barr virus (Y. Li., et al.: Fatty acid synthase expression is induced by the Epstein-Barr virus immediate-early protein BRLF1 and is required for lytic viral gene expression. Journal of Virology 78,8 (2004) 4197-4206), human papilloma virus (L. Louw, et al.: HPV-induced recurrent laryngeal papillomatosis: fatty acid role-players. Asia Pac J Clin Nutr 17 (S1) (2008) 208-211), coxsackievirus B3 (A. Rassmann, et al.: The human fatty acid synthase: A new therapeutic target for coxsackievirus B3-induced diseases? Antiviral Research 76 (2007) 150-158), Rous sarcoma virus (H. Goldfine, et al.: Effects of inhibitors of lipid synthesis on the replication of Rous Sarcoma Virus. A specific effect of cerulenin on the processing of major non-glycosylated viral structural proteins. Biochimica et Biophysica Acta 512 (1978) 229-240), as well as human cytomegalovirus (HCMV), and influenza A virus (J. Munger, et al.: Systems-level metabolic flux profiling identifies fatty acid synthesis as a target for antiviral therapy. Nature Biotechnology 26 (2008) 1 179-1 186).

Taken together, there is growing evidence, that activity of the host's FAS plays an important role in viral infection and viral replication, suggesting FAS as a target for antiviral therapy. The expression of FAS is strongly increased in many cancers and there is evidence that efficient fatty acid synthesis is required for tumor cell survival. Inhibition of FAS has therefore been suggested as a new direction for oncology (Expert Opin. Investig. Drugs 16,1 (2007)1817-1829).

Fatty acids have an essential role in a variety of cellular processes including building blocks for membranes, anchors for targeting membrane proteins, precursors in the synthesis of lipid second messengers and as a medium to store energy, Menendez J S and Lupu R, Fatty acid synthase and the lipogenic phenotype in cancer pathogenesis, Nature Reviews Cancer, 7: 763-777 (2007). Fatty acids can either be obtained from the diet or can be synthesized de novo from carbohydrate precursors. The biosynthesis of the latter is catalyzed by the multi-functional homodimeric FAS. FAS synthesizes long chain fatty acids by using acetyl-CoA as a primer and Malonyl Co-A as a 2 carbon donor, and NADPH as a reducing equivalents (Wakil S J, Lipids, Structure and function of animal fatty acid synthase, 39: 1045-1053 (2004), Asturias F J et al., Structure and molecular organization of mammalian fatty acid synthase, Nature Struct. Mol. Biol. 12:225-232

(2005), Maier T, et al., Architecture of Mammalian Fatty Acid Synthase at 4.5 A Resolution, Science 311 : 1258-1262 (2006).

De novo fatty acid synthesis is active during embryogenesis and in fetal lungs where fatty acids are used for the production of lung surfactant. In adults, most normal human tissues preferentially acquire fatty acids from the diet. Therefore, the level of de novo lipogensis and expression of liopogenic enzymes is low, Weiss L, et al, Fatty-acid biosynthesis in man, a pathway of minor importance. Purification, optimal assay conditions, and organ distribution of fatty-acid synthase. Biological Chemistry Hoppe-Seyler 367(9):905-912 (1986). In contrast, many tumors have high rates of de novo fatty acid synthesis Medes G, et al, Metabolism of Neoplastic Tissue. IV. A Study of Lipid Synthesis in Neoplastic Tissue Slices in Vitro, Can Res, 13:27-29, (1953). FAS has now been shown to be overexpressed in numerous cancer types including prostate, ovary, colon, endometrium lung, bladder, stomach and kidney Kuhajda F P, Fatty-acid synthase and human cancer: new perspectives on its role in tumor biology, Nutrition; 16:202-208 (2000). This differential expression and function of FAS in tumors and normal cells provide an approach for cancer therapy with the potential of a substantial therapeutic window.

Pharmacological and small interference RNA mediated inhibition of FAS has demonstrated a preferential inhibition of cancer cell proliferation. Additionally these inhibitors induce apoptosis in cancers cells in vitro and retard growth in human tumors in murine xenograft models in vivo, Menendez J S and Lupu R, Nature Reviews Cancer, 7: 763-777 (2007). Based upon these findings, FAS is considered a major potential target of antineoplastic intervention.

The invention had the object of finding novel compounds having valuable properties, in particular those which can be used for the preparation of medicaments.

It has been found that the compounds according to the invention and salts thereof have very valuable pharmacological properties while being well tolerated.

The present invention specifically relates to compounds of the formula I which inhibit FASN, to compositions which comprise these compounds, and to processes for the use thereof for the treatment of FASN-induced diseases and complaints.

The compounds of the formula I can furthermore be used for the isolation and investigation of the activity or expression of FASN. In addition, they are particularly suitable for use in diagnostic methods for diseases in connection with unregulated or disturbed FASN activity.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow active agents such as anti IgM to induce a cellular response such as expression of a surface marker, usually between about one hour and one week. In vitro testing can be carried out using cultivated cells from blood or from a biopsy sample. The amount of surface marker expressed is assessed by flow cytometry using specific antibodies recognising the marker.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

PRIOR ART

Spirocyclic piperidine derivatives are described in WO 2012/046642 A1 as FAS inhibitors for the treatment of cancer.

Cyclopentanecarboxamide derivatives are described in WO 2011/048018 A1 as FAS inhibitors for the treatment of obesity and diabetes.

SUMMARY OF THE INVENTION

The invention relates to compounds of the formula I

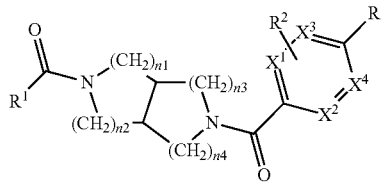

in which $R^1$ denotes A or Cyc, $R^2$ denotes H, F, Cl, Br, OH, CN, $NO_2$, A', OA', SA', $SO_2$Me, COA' or $CONA'_2$, R denotes Ar or Het, $X^1, X^2, X^3, X^4$ each, independently of one another, denote CH or N, A denotes unbranched or branched alkyl with 1-10 C-atoms, wherein two adjacent carbon atoms may form a double bond and/or one or two non-adjacent CH- and/or $CH_2$- groups may be replaced by N—, O—and/or S-atoms and wherein 1-7 H-atoms may be replaced by $R^4$, Cyc denotes cycloalkyl with 3-7 C-atoms, which is unsubstituted or monosubstituted by OH, Hal or A, A' denotes unbranched or branched alkyl with 1-6 C-atoms, wherein 1-5 H-atoms may be replaced by F, $R^4$ denotes F, Cl, Br, OH, CN, $NO_2$, A', OA', SA', $SO_2$Me, COA' or $CONA'_2$, Ar denotes phenyl, which is unsubstituted, or mono-, di-, tri-, tetra- or pentasubstituted by Hal, A, $[C(R^3)_2]_pOR^3$, $[C(R^3)_2]_pN(R^3)_2$, $NO_2$, CN, $[C(R^3)_2]_pCOOR^3$, $[C(R^3)_2]_pN(R^3)_2$, $N(R^3)_2COA$, $NR^3SO_2A$, $[C(R^3)_2]_pSO_2N(R^3)_2$, $S(O)_nA$, $O[C(R^3)_2]_mN(R^3)_2$, NHCOOA, $NHCON(R^3)_2$ and/or COA, $R^3$ denotes H or unbranched or branched alkyl with 1-6 C-atoms, Het denotes a mono- or bicyclic saturated, unsaturated or aromatic heterocycle having 1 to 4 N, O and/or S atoms, which may be unsubstituted or mono-, di-, tri-, tetra- or pentasubstituted by Hal, A, $[C(R^3)_2]_nOR^3$, $[C(R^3)_2]_n N(R^3)_2$, $SR^3$, $NO_2$, CN, $COOR^3$, $CON(R^3)_2$, $NR^3COA$, $NR^3SO_2A$, $SO_2N(R^3)_2$, $S(O)_mA$, $O[C(R^3)_2]_nN(R^3)_2$, NHCOOA, $NHCON(R^3)_2$, CHO, COA, =S, =NH, =NA and/or =O (carbonyl oxygen), Hal denotes F, Cl, Br or I,
n1, n2, n3, n4 each, independently of one another, denote 0, 1 or 2,
m denotes 1, 2 or 3,
n denotes 0, 1 or 2,
p denotes 0, 1, 2, 3 or 4,
with the proviso that only one or two of $X^1$, $X^2$, $X^3$, $X^4$ denote N,
and pharmaceutically acceptable salts, tautomers and stereoisomers thereof, including mixtures thereof in all ratios.

The invention also relates to the optically active forms (stereoisomers), the enantiomers, the racemates, the diastereomers and the hydrates and solvates of these compounds.

Moreover, the invention relates to pharmaceutically acceptable derivatives of compounds of formula I.

The term solvates of the compounds is taken to mean adductions of inert solvent molecules onto the compounds which form owing to their mutual attractive force. Solvates are, for example, mono- or dihydrates or alkoxides.

It is understood, that the invention also relates to the solvates of the salts. The term pharmaceutically acceptable derivatives is taken to mean, for example, the salts of the compounds according to the invention and also so-called prodrug compounds.

As used herein and unless otherwise indicated, the term "prodrug" means a derivative of a compound of formula I that can hydrolyze, oxidize, or otherwise react under biological conditions (in vitro or in vivo) to provide an active compound, particularly a compound of formula I. Examples of prodrugs include, but are not limited to, derivatives and metabolites of a compound of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:
improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution.

The invention relates to the compounds of the formula I and salts thereof and to a process for the preparation of compounds of the formula I and pharmaceutically acceptable salts, solvates, tautomers and stereoisomers thereof, characterised in that
a compound of the formula II

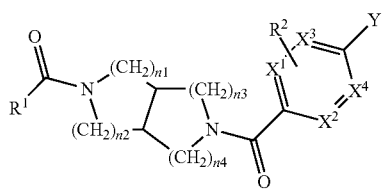

in which $R^1$, $R^2$, $X^1$, $X^2$, $X^3$, $X^4$, n1, n2, n3 and n4 have the meanings indicated in Claim 1, and
Y denotes Br or I,
is reacted with a compound of the formula III

R-L   III in which R has the meaning indicated in Claim 1,
and L denotes a boronic acid or a boronic acid ester group,
in a Suzuki-type coupling,
and/or
a base or acid of the formula I is converted into one of its salts.

Above and below, the radicals $R^1$, $R^2$, R, $X^1$, $X^2$, $X^3$, $X^4$, n1, n2, n3 and n4 have the meanings indicated for the formula I, unless expressly stated otherwise.

A denotes alkyl, this is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methyl-propyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl. Moreover, A denotes preferably $CH_2OCH_3$, $CH_2CH_2OH$ or $CH_2CH_2OCH_3$. Cyc denotes cyclopropyl, cyclobutyl, cyclopentyl, cyclohexyl or cycloheptyl, preferably unsubstituted or monosubstituted by OH, Hal or A.

$R^2$ preferably denotes H.

$R^3$ preferably denotes H, methyl, ethyl, propyl, isopropyl, butyl, pentyl or hexyl, particularly preferably H or methyl.

n1, n2, n3, n4 very particularly preferably denote 1.

Ar denotes preferably o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-methoxyphenyl, o-, m- or p-ethoxyphenyl, o-, m- or p-ethoxycarbonyl-phenyl, o-, m- or p-(N, N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-cyanophenyl, o-, m- or p-carboxyphenyl, o-, m- or p-methoxycarbonylphenyl, o-, m- or p-formylphenyl, o-, m- or p-acetylphenyl, o-, m- or p-aminosulfonylphenyl, o-, m- or p-[2-(morpholin-4-yl)ethoxy]phenyl, o-, m- or p-[3-(N,N-diethylamino)propoxy]phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylamino-phenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodo-phenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar furthermore preferably denotes phenyl, which is monosubstituted by Hal, A or $[C(R^2)_2]_p COOR^2$.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7- benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-iso-quinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4-, -5-yl or 2,1,3-benzoxadiazol-5-yl, azabicyclo[3.2.1]octyl or dibenzofuranyl.

The heterocyclic radicals may also be partially or fully hydrogenated. Irrespective of further substitutions, Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3, 4-tetrahydro-1-,-2-,-3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-di-hydrobenzoxazolyl, 2,3-dihydrobenzimidazolyl, 1,3-dihydroindole, 2-oxo-1,3-dihydroindole or 2-oxo-2,3-dihydrobenzimidazolyl.

Het preferably denotes a mono- or bicyclic aromatic heterocycle having 1 to 4 N, O and/or S atoms, which may be unsubstituted or mono-or disubstituted by Hal or A.

Het furthermore preferably denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzoxazolyl, benzothiazolyl, benzimidazolyl, benzotriazolyl, indolyl, benzo-1,3-dioxolyl, benzodioxanyl, benzothiadiazolyl, indazolyl, benzofuranyl, quinolyl or isoquinolyl, which may be unsubstituted or mono-or disubstituted by Hal or A. Het very particularly preferably denotes benzoxazolyl, benzothiazolyl, benzimidazolyl, benzotriazolyl, indolyl, benzo-1,3-dioxolyl, benzodioxanyl, benzothiadiazolyl, indazolyl, benzofuranyl, quinolyl or isoquinolyl.

Hal preferably denotes F, Cl or Br, but also I, particularly preferably F or Cl.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Ik, which conform to the formula I and in which the radicals not designated in greater detail have the meaning indicated for the formula I, but in which in Ia $X^1$, $X^3$ denote CH,
  $X^2$, $X^4$ denote N;
in Ib $X^1$, $X^2$, $X^3$, $X^4$ denote CH,
in Ic $X^1$, $X^3$, $X^4$ denote CH,
  $X^2$ denotes N;
in Id $X^1$, $X^2$, $X^3$ denote CH,
  $X^4$ denotes N;
in Ie $X^1$, $X^2$ denote CH,
  $X^3$, $X^4$ denote N;
in If $X^3$, $X^4$ denote CH,
  $X^1$, $X^2$ denote N;
in Ig $R^2$ denotes H;
in Ih Het denotes a mono- or bicyclic aromatic heterocycle having 1 to 4 N, O and/or S atoms, which may be unsubstituted or mono-or disubstituted by Hal or A;
in Ii Het denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzoxazolyl, benzothiazolyl, benzimidazolyl, benzotriazolyl, indolyl, benzo-1,3-dioxolyl, benzodioxanyl, benzothiadiazolyl, indazolyl, benzofuranyl, quinolyl or isoquinolyl, which may be unsubstituted or mono-or disubstituted by Hal or A;

in Ij Het denotes benzoxazolyl, benzothiazolyl, benzimidazolyl, benzotriazolyl, indolyl, benzo-1,3-dioxolyl, benzodioxanyl, benzothiadiazolyl, indazolyl, benzofuranyl, quinolyl or isoquinolyl;

in Ik $R^1$ denotes A or Cyc, $R^2$ denotes H,

R denotes Het, $X^1, X^2, X^3, X^4$ each, independently of one another, denote CH or N, A denotes unbranched or branched alkyl with 1-6 C-atoms, wherein 1-5 H-atoms may be replaced by F, Cyc denotes cycloalkyl with 3-7 C-atoms, Het denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzoxazolyl, benzothiazolyl, benzimidazolyl, benzotriazolyl, indolyl, benzo-1, 3-dioxolyl, benzodioxanyl, benzothiadiazolyl, indazolyl, benzofuranyl, quinolyl or isoquinolyl, which may be unsubstituted or mono-or disubstituted by Hal or A, Hal denotes F, Cl, Br or I, n1, n2, n3, n4 each, independently of one another, denote 0, 1 or 2, with the proviso that only one or two of $X^1, X^2, X^3, X^4$ denote N, and pharmaceutically acceptable salts, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The starting compounds of the formulae II and III are generally known. If they are novel, however, they can be prepared by methods known per se.

Compounds of the formula I can preferably be obtained by reacting a compound of the formula II with a compound of the formula III. In the compounds of the formula III, L preferably denotes

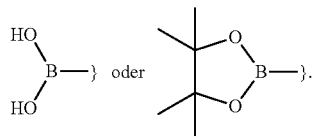

The reaction is generally carried out under conditions of a Suzuki-type coupling.

Depending on the conditions used, the reaction time is between a few minutes and 14 days, the reaction temperature is between about −30° and 160°, normally between 20° and 160°, in particular between about 100° and about 160°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to dioxane.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, formate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine(benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine(tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$) alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Isotopes

There is furthermore intended that a compound of the formula I includes isotope-labelled forms thereof. An isotope-labelled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. A compound of the formula I, a prodrug, thereof or a pharmaceutically acceptable salt of either which contains one or more of the above-mentioned isotopes and/or other isotopes of other atoms is intended to be part of the present invention. An isotope-labelled compound of the formula I can be used in a number of beneficial ways. For example, an isotope-labelled compound of the formula I into which, for example, a radioisotope, such as $^3H$ or $^{14}C$, has been incorporated is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of the formula I has therapeutic advantages owing to the higher metabolic stability of this isotope-labelled compound. Higher metabolic stability translates directly into an increased in vivo half-life or lower dosages, which under most circumstances would represent a preferred embodiment of the present invention. An isotope-labelled compound of the formula I can usually be prepared by carrying out the procedures disclosed in the synthesis schemes and the related description, in the example part and in the preparation part in the present text, replacing a non-isotope-labelled reactant by a readily available isotope-labelled reactant. Deuterium ($^2H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange.

Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a compound of the formula I that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The invention furthermore relates to medicaments comprising at least one compound of the formula I and/or pharmaceutically acceptable salts, tautomers and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and pharmaceutically acceptable salts, tautomers and stereoisomers thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the pharmaceutically acceptable salts, tautomers and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, polyepsiloncaprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

A combined treatment of this type can be achieved with the aid of simultaneous, consecutive or separate dispensing of the individual components of the treatment. Combination products of this type employ the compounds according to the invention.

The invention furthermore relates to medicaments comprising at least one compound of the formula I and/or pharmaceutically acceptable salts, tauotmers and stereoisomers thereof, including mixtures thereof in all ratios, and at least one further medicament active ingredient.

The invention also relates to a set (kit) consisting of separate packs of (a) an effective amount of a compound of the formula I and/or pharmaceutically acceptable salts, tautomers and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically acceptable salts, solvates and stereoisomers thereof, including mixtures thereof in all ratios, and an effective amount of a further medicament active ingredient in dissolved or lyophilised form.

"Treating" as used herein, means an alleviation, in whole or in part, of symptoms associated with a disorder or disease, or slowing, or halting of further progression or worsening of those symptoms, or prevention or prophylaxis of the disease or disorder in a subject at risk for developing the disease or disorder.

The term "effective amount" in connection with a compound of formula (I) can mean an amount capable of alleviating, in whole or in part, symptoms associated with a disorder or disease, or slowing or halting further progression or worsening of those symptoms, or preventing or providing prophylaxis for the disease or disorder in a subject having or at risk for developing a disease disclosed herein, such as inflammatory conditions, immunological conditions, cancer or metabolic conditions.

In one embodiment an effective amount of a compound of formula (I) is an amount that inhibits a tankyrase in a cell, such as, for example, in vitro or in vivo. In some embodiments, the effective amount of the compound of formula (I) inhibits tankyrase in a cell by 10%, 20%, 30%, 40%, 50%, 60%, 70%, 80%, 90% or 99%, compared to the activity of tankyrase in an untreated cell. The effective amount of the compound of formula (I), for example in a pharmaceutical composition, may be at a level that will exercise the desired effect; for example, about 0.005 mg/kg of a subject's body weight to about 10 mg/kg of a subject's body weight in unit dosage for both oral and parenteral administration.

Use

The present compounds of formula I are useful for treating or preventing cardiovascular disorders and/or conditions. Treatment with the present compounds is expected to lower the cardiovascular morbidity and mortality associated with atherosclerosis due to their antidyslipidaemic as well as anti-inflammatory properties. The cardiovascular disease conditions include macro-angiopathies of various internal organs causing myocardial infarction, congestive heart failure, cerebrovascular disease and peripheral arterial insufficiency of the lower extremities. Because of their insulin sensitizing effect the compounds of formula I are also expected to prevent or delay the development of type 2 diabetes from the metabolic syndrome and diabetes of pregnancy. Therefore the development of long-term complications associated with chronic hyperglycaemia in diabetes mellitus, such as the micro-angiopathies causing renal disease, retinal damage and peripheral vascular disease of the lower limbs, is expected to be delayed.

In addition the present compounds of formula I are useful for treating or preventing inflammatory and/or neurodegenerative disorders and/or conditions. Examples of such disorders or conditions are polycystic ovarian syndrome and states of inflammatory disease including neurodegenerative disorders such as mild cognitive impairment, Alzheimer's disease, Parkinson's disease and multiple sclerosis.

The compounds of the present invention may also be useful for decreasing sebum production in sebaceous glands of the skin following systemic or topical application. Diseases of the sebaceous gland are acne, seborrhea, sebaceoma and sebaceous carcinoma. The pathogenesis of acne involves lipid (over)production by the sebaceous gland and therefore compound of the present invention may be particularly useful in the treatment of acne. Moreover, compounds of formula I may be useful as antimycobacterial agents in the treatment of mycobacterial infections, such as e.g. *tuberculosis*. Compounds of the invention may be useful to treat conditions associated with viral infection like e.g. Hepatitis C, AIDS, Polio, Influenza, warts.

Examples of inflammatory diseases include rheumatoid arthritis, psoriasis, contact dermatitis, delayed hypersensitivity reaction and the like.

Also encompassed is the use of the compounds of the formula I and/or pharmaceutically acceptable salts, tautomers and stereoisomers thereof for the preparation of a medicament for the treatment or prevention of a FASN-induced disease or a FASN-induced condition in a mammal, in which to this method a therapeutically effective amount of a compound according to the invention is administered to a sick mammal in need of such treatment. The therapeutic amount varies according to the specific disease and can be determined by the person skilled in the art without undue effort.

The expression "FASN-induced diseases or conditions" refers to pathological conditions that depend on the activity of FASN. Diseases associated with FASN activity include cancer, multiple sclerosis, cardiovascular diseases, central nervous system injury and different forms of inflammation.

The present invention specifically relates to compounds of the formula I and pharmaceutically acceptable salts, tautomers and stereoisomers thereof, including mixtures thereof in all ratios, for the use for the treatment of diseases in which the inhibition, regulation and/or modulation inhibition of FASN plays a role.

The present invention specifically relates to compounds of the formula I and pharmaceutically acceptable salts, tautomers and stereoisomers thereof, including mixtures thereof in all ratios, for the use for the inhibition of FASN.

The present invention specifically relates to compounds of the formula I and pharmaceutically acceptable salts, tautomers and stereoisomers thereof, including mixtures thereof in all ratios, for the use for the treatment of cancer, multiple sclerosis, cardiovascular diseases, central nervous system injury and different forms of inflammation.

The present invention specifically relates to methods for treating or preventing cancer, multiple sclerosis, cardiovascular diseases, central nervous system injury and different forms of inflammation, comprising administering to a subject in need thereof an effective amount of a compound of formula I or a pharmaceutically acceptable salt, tautomer, stereoisomer or solvate thereof.

Representative cancers that compounds of formula I are useful for treating or preventing include, but are not limited to, cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, brain, central nervous system, solid tumors and blood-borne tumors.

Moreover, representative cancers that compounds of formula I are useful for treating or preventing include cancer of brain (gliomas), glioblastomas, leukemias, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone and thyroid.

Representative cardiovascular diseases that compounds of formula I are useful for treating or preventing include, but are not limited to, restenosis, atherosclerosis and its consequences such as stroke, myocardial infarction, ischemic damage to the heart, lung, gut, kidney, liver, pancreas, spleen or brain.

The present invention relates to a method of treating a proliferative, autoimmune, anti inflammatory or infectious disease disorder that comprises administering to a subject in need thereof a therapeutically effective amount of a compound of formula I.

Preferably, the present invention relates to a method wherein the disease is a cancer.

Particularly preferable, the present invention relates to a method wherein the disease is a cancer, wherein administration is simultaneous, sequential or in alternation with administration of at least one other active drug agent.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic/DNA-damaging agents and combinations thereof, as used in medical oncology, such as alkylating agents (for example cis-platin, carboplatin, cyclophosphamide, nitrogen mustard, melphalan, chloroambucil, busulphan and nitrosoureas); anti-metabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines, like adriamycin, bleomycin, doxorubicin, daunomycin, epirubicin, idarubicin, mitomycin-C, dactinomycin and mithramycin); antimitotic agents (for example vinca alkaloids, like vincristine, vinblastine, vindesine and vinorelbine, and taxoids, like taxol and taxotere); topoisomerase inhibitors (for example epipodophyllotoxins, like etoposide and teniposide, amsacrine, topotecan, irinotecan and camptothecin) and cell-differentiating agents (for example all-trans-retinoic acid, 13-cis-retinoic acid and fenretinide);

(ii) cytostatic agents, such as antioestrogens (for example tamoxifen, toremifene, raloxifene, droloxifene and iodoxyfene), oestrogen receptor downregulators (for example fulvestrant), antiandrogens (for example bicalutamide, flutamide, nilutamide and cyproterone acetate), LHRH antagonists or LHRH agonists (for example goserelin, leuprorelin and buserelin), progesterones (for example megestrol acetate), aromatase inhibitors (for example as anastrozole, letrozole, vorazole and exemestane) and inhibitors of 5α-reductase, such as finasteride;

(iii) agents which inhibit cancer cell invasion (for example metalloproteinase inhibitors, like marimastat, and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6- (3-morpholinopropoxy)quinazolin-4-amine (gefitinib, AZD1839), N-(3-ethynyl-phenyl)-6,7-bis(2-methoxyethoxy) quinazolin-4-amine (erlotinib, OSI-774) and 6-acrylamido-N-(3-chloro-4-fluorophenyl)-7-(3-morpholinopropoxy)-quinazolin-4-amine (CI 1033)), for example inhibitors of the platelet-derived growth factor family and for example inhibitors of the hepatocyte growth factor family;

(v) antiangiogenic agents, such as those which inhibit the effects of vascular endothelial growth factor, (for example the anti-vascular endothelial cell growth factor antibody bevacizumab [Avastin™], compounds such as those disclosed in published international patent applications WO 97/22596, WO 97/30035, WO 97/32856 and WO 98/13354) and compounds that work by other mechanisms (for example linomide, inhibitors of integrin αvβ3 function and angiostatin);

(vi) vessel-damaging agents, such as combretastatin A4 and compounds disclosed in international patent applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-Ras antisense;

(viii) gene therapy approaches, including, for example, approaches for replacement of aberrant genes, such as aberrant p53 or aberrant BRCA1 or BRCA2, GDEPT (gene-directed enzyme pro-drug therapy) approaches, such as those using cytosine deaminase, thymidine kinase or a bacterial nitroreductase enzyme, and approaches for increasing patient tolerance to chemotherapy or radiotherapy, such as multi-drug resistance gene therapy; and (ix) immunotherapy approaches, including, for example, ex-vivo and in-vivo approaches for increasing the immunogenicity of patient tumour cells, such as transfection with cytokines, such as interleukin 2, interleukin 4 or granulocyte-macrophage colony stimulating factor, approaches for decreasing T-cell anergy, approaches using transfected immune cells, such as cytokine-transfected dendritic cells, approaches using cytokine-transfected tumour cell lines, and approaches using anti-idiotypic anti-bodies.

The medicaments from Table 1 below are preferably, but not exclusively, combined with the compounds of the formula I.

TABLE 1

| Alkylating agents | Cyclophosphamide | Lomustine |
|---|---|---|
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aeterna) |
| | Carboxyphthalatoplatinum | Satraplatin (Johnson Matthey) |
| | Tetraplatin | BBR-3464 |
| | Ormiplatin | (Hoffmann-La Roche) |
| | Iproplatin | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | Pixantrone (Novuspharma) | BNP-1350 (BioNumerik) |
| | Rebeccamycin analogue (Exelixis) | CKD-602 (Chong Kun Dang) |
| | BBR-3576 (Novuspharma) | KW-2170 (Kyowa Hakko) |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | Epirubicin | Bleomycin sulfate (Blenoxan) |
| | Therarubicin | Bleomycinic acid |
| | Idarubicin | Bleomycin A |
| | Rubidazon | Bleomycin B |
| | Plicamycinp | Mitomycin C |
| | Porfiromycin | MEN-10755 (Menarini) |
| | Cyanomorpholinodoxo-rubicin | GPX-100 (Gem Pharmaceuticals) |
| | Mitoxantron (Novantron) | |
| Antimitotic agents | Paclitaxel | SB 408075 (GlaxoSmithKline) |
| | Docetaxel | E7010 (Abbott) |
| | Colchicine | PG-TXL (Cell Therapeutics) |
| | Vinblastine | IDN 5109 (Bayer) |
| | Vincristine | A 105972 (Abbott) |
| | Vinorelbine | A 204197 (Abbott) |
| | Vindesine | LU 223651 (BASF) |
| | Dolastatin 10 (NCI) | D 24851 (ASTA Medica) |
| | Rhizoxin (Fujisawa) | ER-86526 (Eisai) |
| | Mivobulin (Warner-Lambert) | Combretastatin A4 (BMS) |
| | Cemadotin (BASF) | Isohomohalichondrin-B (PharmaMar) |
| | RPR 109881A (Aventis) | ZD 6126 (AstraZeneca) |
| | TXD 258 (Aventis) | PEG-Paclitaxel (Enzon) |
| | Epothilone B (Novartis) | AZ10992 (Asahi) |
| | T 900607 (Tularik) | !DN-5109 (Indena) |
| | T 138067 (Tularik) | |
| | Cryptophycin 52 (Eli Lilly) | |

TABLE 1-continued

| Category | Column 2 | Column 3 |
|---|---|---|
| | Vinflunine (Fabre) | AVLB (Prescient NeuroPharma) |
| | Auristatin PE (Teikoku Hormone) | Azaepothilon B (BMS) |
| | BMS 247550 (BMS) | BNP- 7787 (BioNumerik) |
| | BMS 184476 (BMS) | CA-4-prodrug (OXiGENE) |
| | BMS 188797 (BMS) | Dolastatin-10 (NrH) |
| | Taxoprexin (Protarga) | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | |
| | MS-209 (Schering AG) | Biricodar dicitrate (Vertex) |
| Histone acetyl transferase inhibitors | Tacedinaline (Pfizer) | Pivaloyloxymethyl butyrate (Titan) |
| | SAHA (Aton Pharma) | |
| | MS-275 (Schering AG) | Depsipeptide (Fujisawa) |
| Metalloproteinase inhibitors | Neovastat (Aeterna Laboratories) | CMT -3 (CollaGenex) |
| | | BMS-275291 (Celltech) |
| Ribonucleoside reductase inhibitors | Marimastat (British Biotech) | Tezacitabine (Aventis) |
| | Gallium maltolate (Titan) | Didox (Molecules for Health) |
| | Triapin (Vion) | |
| TNF-alpha agonists/ antagonists | Virulizin (Lorus Therapeutics) | Revimid (Celgene) |
| | CDC-394 (Celgene) | |
| Endothelin-A receptor antagonists | Atrasentan (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immunomodulators | Interferon | Dexosome therapy (Anosys) |
| | Oncophage (Antigenics) | |
| | GMK (Progenics) | Pentrix (Australian Cancer Technology) |
| | Adenocarcinoma vaccine (Biomira) | JSF-154 (Tragen) |
| | CTP-37 (AVI BioPharma) | Cancer vaccine (Intercell) |
| | JRX-2 (Immuno-Rx) | Norelin (Biostar) |
| | PEP-005 (Peplin Biotech) | BLP-25 (Biomira) |
| | Synchrovax vaccines (CTL Immuno) | MGV (Progenics) |
| | Melanoma vaccine (CTL Immuno) | !3-Alethin (Dovetail) |
| | p21-RAS vaccine (GemVax) | CLL-Thera (Vasogen) |
| Hormonal and antihormonal agents | Oestrogens | Prednisone |
| | Conjugated oestrogens | Methylprednisolone |
| | Ethynyloestradiol | Prednisolone |
| | chlorotrianisene | Aminoglutethimide |
| | Idenestrol | Leuprolide |
| | Hydroxyprogesterone caproate | Goserelin |
| | | Leuporelin |
| | Medroxyprogesterone | Bicalutamide |
| | Testosterone | Flutamide |
| | Testosterone propionate | Octreotide |
| | Fluoxymesterone | Nilutamide |
| | Methyltestosterone | Mitotan |
| | Diethylstilbestrol | P-04 (Novogen) |
| | Megestrol | 2-Methoxyoestradiol (EntreMed) |
| | Tamoxifen | |
| | Toremofin | Arzoxifen (Eli Lilly) |
| | Dexamethasone | |

TABLE 1-continued

| | | |
|---|---|---|
| Photodynamic agents | Talaporfin (Light Sciences) Theralux (Theratechnologies) Motexafin-Gadolinium (Pharmacyclics) | Pd-Bacteriopheophorbid (Yeda) Lutetium-Texaphyrin (Pharmacyclics) Hypericin |
| Tyrosine kinase inhibitors | Imatinib (Novartis) Leflunomide(Sugen/ Pharmacia) ZD1839 (AstraZeneca) Erlotinib (Oncogene Science) Canertjnib (Pfizer) Squalamine (Genaera) SU5416 (Pharmacia) SU6668 (Pharmacia) ZD4190 (AstraZeneca) ZD6474 (AstraZeneca) Vatalanib (Novartis) PKI166 (Novartis) GW2016 (GlaxoSmithKline) EKB-509 (Wyeth) EKB-569 (Wyeth) | Kahalide F (PharmaMar) CEP-701 (Cephalon) CEP-751 (Cephalon) MLN518 (Millenium) PKC412 (Novartis) Phenoxodiol O Trastuzumab (Genentech) C225 (ImClone) rhu-Mab (Genentech) MDX-H210 (Medarex) 2C4 (Genentech) MDX-447 (Medarex) ABX-EGF (Abgenix) IMC-1C11 (ImClone) |
| Various agents | SR-27897 (CCK-A inhibitor, Sanofi-Synthelabo) Tocladesine (cyclic AMP agonist, Ribapharm) Alvocidib (CDK inhibitor, Aventis) CV-247 (COX-2 inhibitor, Ivy Medical) P54 (COX-2 inhibitor, Phytopharm) CapCell ™ (CYP450 stimulant, Bavarian Nordic) GCS-IOO (gal3 antagonist, GlycoGenesys) G17DT immunogen (gastrin inhibitor, Aphton) Efaproxiral (oxygenator, Allos Therapeutics) PI-88 (heparanase inhibitor, Progen) Tesmilifen (histamine antagonist, YM BioSciences) Histamine (histamine H2 receptor agonist, Maxim) Tiazofurin (IMPDH inhibitor, Ribapharm) Cilengitide (integrin antagonist, Merck KGaA) SR-31747 (IL-1 antagonist, Sanofi-Synthelabo) CCI-779 (mTOR kinase inhibitor, Wyeth) Exisulind (PDE-V inhibitor, Cell Pathways) CP-461 (PDE-V inhibitor, Cell Pathways) AG-2037 (GART inhibitor, Pfizer) WX-UK1 (plasminogen activator inhibitor, Wilex) PBI-1402 (PMN stimulant, ProMetic LifeSciences) Bortezomib (proteasome inhibitor, Millennium) SRL-172 (T-cell stimulant, SR Pharma) TLK-286 (glutathione-S transferase inhibitor, Telik) PT-100 (growth factor agonist, Point Therapeutics) Midostaurin (PKC inhibitor, Novartis) Bryostatin-1 (PKC stimulant, GPC Biotech) | BCX-1777 (PNP inhibitor, BioCryst) Ranpirnase (ribonuclease stimulant, Alfacell) Galarubicin (RNA synthesis inhibitor, Dong-A) Tirapazamine (reducing agent, SRI International) N-Acetylcysteine (reducing agent, Zambon) R-Flurbiprofen (NF-kappaB inhibitor, Encore) 3CPA (NF-kappaB inhibitor, Active Biotech) Seocalcitol (vitamin D receptor agonist, Leo) 131-I-TM-601 (DNA antagonist, TransMolecular) Eflornithin (ODC inhibitor, ILEX Oncology) Minodronic acid (osteoclast inhibitor, Yamanouchi) Indisulam (p53 stimulant, Eisai) Aplidin (PPT inhibitor, PharmaMar) Rituximab (CD20 antibody, Genentech) Gemtuzumab (CD33 antibody, Wyeth Ayerst) PG2 (haematopoiesis promoter, Pharmagenesis) Immunol ™ (triclosan mouthwash, Endo) Triacetyluridine (uridine prodrug, Wellstat) SN-4071 (sarcoma agent, Signature BioScience) TransMID-107 ™ (immunotoxin, KS Biomedix) PCK-3145 (apoptosis promoter, Procyon) Doranidazole (apoptosis promoter, Pola) CHS-828 (cytotoxic agent, Leo) Trans-retinic acid (differentiator, NIH) MX6 (apoptosis promoter, MAXIA) Apomine (apoptosis promoter, ILEX Oncology) |

TABLE 1-continued

| | |
|---|---|
| CDA-II (apoptosis promoter, Everlife) | Urocidin (apoptosis promoter, Bioniche) |
| SDX-101 (apoptosis promoter, Salmedix) | Ro-31-7453 (apoptosis promoter, La Roche) |
| Ceflatonin (apoptosis promoter, ChemGenex) | Brostallicin (apoptosis promoter, Pharmacia) |

The following abbreviations refer respectively to the definitions below:

aq (aqueous), h (hour), g (gram), L (liter), mg (milligram), MHz (Megahertz), min. (minute), mm (millimeter), mmol (millimole), mM (millimolar), m.p. (melting point), eq (equivalent), mL (milliliter), L (microliter), ACN (acetonitrile), AcOH (acetic acid), CDCl$_3$ (deuterated chloroform), CD$_3$OD (deuterated methanol), CH$_3$CN (acetonitrile), c-hex (cyclohexane), DCC (dicyclohexyl carbodiimide), DCM (dichloromethane), DIC (diisopropyl carbodiimide), DIEA (diisopropylethyl-amine), DMF (dimethylformamide), DMSO (dimethylsulfoxide), DMSO-d$_6$ (deuterated dimethylsulfoxide), EDC (1-(3-dimethyl-amino-propyl)-3-ethyl-carbodiimide), ESI (Electro-spray ionization), EtOAc (ethyl acetate), Et$_2$O (diethyl ether), EtOH (ethanol), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), K$_2$CO$_3$ (potassium carbonate), LC (Liquid Chromatography), MeOH (methanol), MgSO$_4$ (magnesium sulfate), MS (mass spectrometry), MTBE (Methyl tert-butyl ether), NaHCO$_3$ (sodium bicarbonate), NaBH$_4$ (sodium borohydride), NMM (N-methyl morpholine), NMR (Nuclear Magnetic Resonance), PyBOP (benzotriazole-1-yl-oxy-tris-pyrrolidino-phosphonium hexafluorophosphate), RT (room temperature), Rt (retention time), SPE (solid phase extraction), TBTU (2-(1-H-benzotriazole-1-yl)-1,1,3,3-tetramethyluromium tetrafluoro borate), TEA (triethylamine), TFA (trifluoroacetic acid), THF (tetrahydrofuran), TLC (Thin Layer Chromatography), UV (Ultraviolet).

Description of the in vitro Assays
Abbreviations:
GST=Glutathione-S-transferase
FRET=Fluorescence resonance energy transfer
HTRF®=(homogenous time resolved fluorescence)
HEPES=4-(2-hydroxyethyl)-1-piperazine ethanesulfonic acid buffer
DTT=Dithiothreitol
BSA=bovine serum albumin
CHAPS=detergent;
CHAPS=3[(3-cholamidopropyl)dimethylammonio]-1-propanesulfonate Biochemical Activity Testing of Human Fatty Acid Synthase FASN Fatty acid synthase FASN is a multifunctional enzyme with seven catalytic activities thereby synthesising long chain fatty acids especially palmitoyl-CoA in the presence of co-factor NADPH starting from the substrates acetyl-CoA and malonyl-CoA. The reductive synthesis is realized by the oxidation of NADPH to NADP. Since NADPH has a high fluorescence intensity quantum yield compared to NADP with excitation at 340 nm and emission at 460 nm, the reaction can be monitored via the decrease in fluorescence intensity. The biochemical FASN activity testing was performed as 384 well two-time-point kinetic fluorescence intensity assay format in Greiner low volume medium binding 384-well black microtiter plates in a total assay volume of 8 µl and was used for high throughput screen. In each well 3 µl 40 nM human recombinant full-length fatty acid synthase (produced in-house in SF9 cells) were dispensed in the following assay buffer: 50 mM potassium phosphate buffer pH 7.0, 0.005% (w/v) BSA, 2 mM Glutathione, 0.02% Tween-20. Then 2 µl of 200 µM NADPH in assay buffer were added, followed by the addition of the test compounds in 10 dilution concentrations starting with 30 µM (final concentration) to get a final DMSO content of 1% (v/v). The mixture was incubated for at least 15 min at room temperature. After the pre-incubation the enzymatic reaction was started by the addition of 2 µl substrate solution (80 µM acetyl-CoA, 240 µM malonyl-CoA). A first fluorescence intensity measurement (time point one) was performed with an Envision multimode reader (Perkin Elmer LAS Germany GmbH) at excitation wavelength 340 nm (lamp mode) and emission wavelength 460 nm. The reaction was incubated for 30 minutes at room temperature. After this the fluorescence intensity was measured again in the Envision using the same parameters as described above (second time point measurement). The data were analysed by subtracting the first time point measurement value from the second time point measurement value (after the enzymatic reaction). The differences of the emission signals were determined. These reflect directly the conversion rate of NADPH. The full value used was the inhibitor-free reaction. A pharmacological zero value was used like GSK837149A (Sigma-Aldrich) in a final concentration of 5-10 µM. The inhibitory values (IC50) were determined using either the program Symyx Assay Explorer® or Condosseo® from GeneData.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the residue is purified by chromatography on silica gel and/or by crystallisation. Rf values on silica gel; eluent: ethyl acetate/methanol 9:1.

HPLC/MS Conditions A
column: Chromolith PerformanceROD RP-18e, 100×3 mm$^2$
gradient: A:B=99:1 to 0:100 in 1.8 min
flow rate: 2.0 ml/min
eluent A: water+0.05% formic acid
eluent B: acetonitrile+0.04% formic acid
wavelength: 220 nm
mass spectroscopy: positive mode HPLC/MS Conditions B
column: Chromolith PerformanceROD RP-18e, 100×3 mm$^2$
gradient: A:B=99:1 to 0:100 in 3.5 min
flow rate: 2.0 ml/min
eluent A: water+0.05% formic acid
Eluent B: acetonitrile+0.04% formic acid
wavelength: 220 nm
mass spectroscopy: positive mode

$^1$H NMR was recorded on Bruker DPX-300, DRX-400 or AVII-400 spectrometer, using residual signal of deuterated solvent as internal reference. Chemical shifts (δ) are reported in ppm relative to the residual solvent signal (δ=2.49 ppm for $^1$H NMR in DMSO-d$_6$). $^1$H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

The microwave chemistry is performed on a single mode microwave reactor Emrys™ Optimiser from Personal Chemistry.

EXAMPLE 1

Synthesis of 1-[5-(4-isoquinolin-6-yl-benzoyl)-hexahydro-pyrrolo[3,4-c]pyrrol-2-yl]-propan-1-one ("A1")

1.3 (4-Bromo-phenyl)-(hexahydro-pyrrolo[3,4-c]pyrrol-2-yl)-methanone hydrochloride (300 mg; 0.9 mmol) is dissolved in 5 ml of DCM, N-ethyldiiso-propylamine for synthesis (0.46 ml; 2.7 mmol) is added and then cooled to 0° C. Propionyl chloride for synthesis (0.095 ml; 1.09 mmol) is added dropwise followed by stirring at RT for 14 h. The reaction mixture is separated between DCM and water. The organic layer is separated, dried over MgSO4, filtered off and then reduced to dryness under vacuo to afford 316 mg (99.5%) 1-[5-(4-bromo-benzoyl)-hexahydro-pyrrolo[3,4-c]pyrrol-2-yl]-propan-1-one 3 as a brown oil.

1.4 1-[5-(4-Bromo-benzoyl)-hexahydro-pyrrolo[3,4-c]pyrrol-2-yl]-propan-1-one (100 mg; 0.285 mmol) and iso-

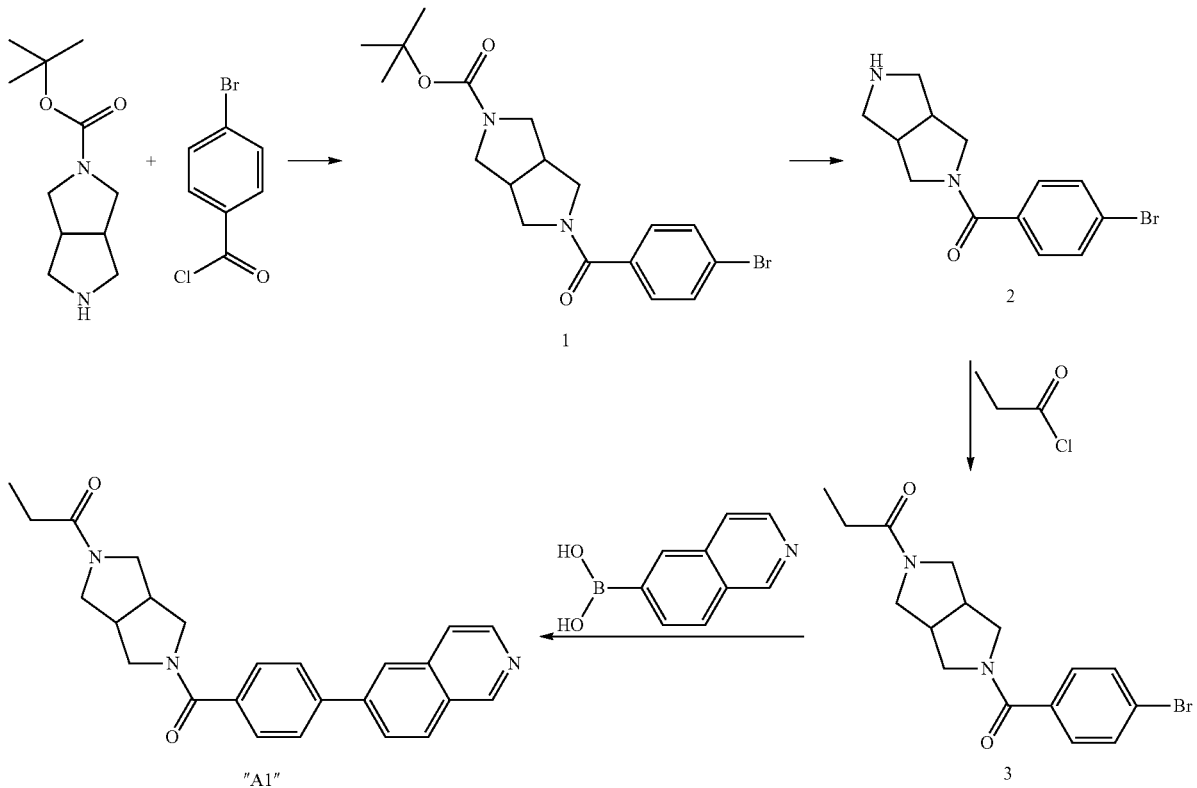

1.1 tert-Butyl hexahydropyrrolo[3,4-c]pyrrole-2(1H)-carboxylate (0.65 g; 3.06 mmol) is dissolved in 20 ml of DCM. N-Ethyldiisopropylamine for synthesis (1.56 ml; 9.19 mmol) is added and the mixture cooled to 0° C. Now 4-bromobenzoyl chloride for synthesis (0.74 g; 3.37 mmol) is dissolved in 10 ml of DCM and added dropwise to the reaction, followed by stirring at RT for 14 h. The reaction mixture is extracted with 50 ml of water. The organic layer is separated, dried over MgSO$_4$, filtered off and then reduced to dryness under vacuo to afford 1.10 g (90.9%) 5-(4-bromo-benzoyl)-hexahydro-pyrrolo[3,4-c]pyrrole-2-carboxylic acid tert-butyl ester 1 as a slight orange oil.

1.2 5-(4-Bromo-benzoyl)-hexahydro-pyrrolo[3,4-c]pyrrole-2-carboxylic acid tert-butyl ester (1.1 g; 2.78 mmol) is dissolved in 15 ml of HCl/Isopropanol (5-6N) and then stirred at RT for 2 hrs. The reaction mixture is reduced to dryness under vacuo to yield 0.90 g (97.5%) (4-bromo-phenyl)-(hexahydro-pyrrolo[3,4-c]pyrrol-2-yl)-methanone 2.

quinolin-6-ylboronic acid (55.2 mg; 0.31 mmol) are dissolved in 1,4-dioxane dried (max. 0.005% H$_2$O), Seccosolv® (5.0 ml; 0.058 mol) and the mixture is purged with nitrogen for 5 minutes. Sodium carbonate anhydrous (90.6 mg, 0.86 mmol) and bis(triscyclohexyl-phosphine)-palladium(II) dichloride, 99% (6.4 mg, 8.7 µM) are added and the reaction mixture is heated to 150° C. for 90 min under microwave. The mixture is extracted with ethyl acetate/water. The organic layer is dried over MgSO$_4$, filtered off and evaporated in vacuo. The product is purified on prep. HPLC to afford 56 mg (49%) 1-[5-(4-isoquinolin-6-yl-benzoyl)-hexahydro-pyrrolo[3,4-c]pyrrol-2-yl]-propan-1-one ("A1") as a white solid;

$^1$H NMR (400 MHz, DMSO-d$_6$, TFA-d$_1$) δ [ppm] 9.96 (s, 1H), 8.75-8.65 (m, 3H), 8.57 (d, J=6.5 Hz, 1H), 8.43 (dd, J=8.7 Hz, J=1.2 Hz, 1H), 8.04 (d, J=8.3 Hz, 2H), 7.78 (d, J=8.3 Hz, 2H), 3.92-3.21 (m, 8H), 3.12-2.87 (m, 2H), 2.39-2.20 (m, 2H), 1.10-0.99 (m, 3H).

The following compounds are obtained analogously

1-[5-(4-benzofuran-6-yl-benzoyl)-hexahydro-pyrrolo[3,4-c]pyrrol-2-yl]-propan-1-one ("A2)

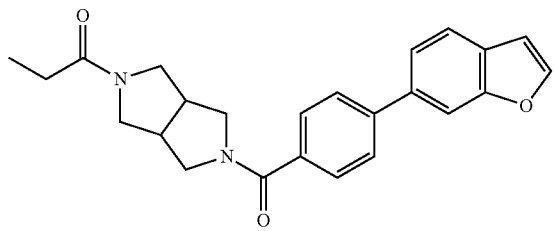 [SMILES: CCC(=O)N1CC2CN(C(=O)c3ccc(-c4ccc5ccoc5c4)cc3)CC2C1]

¹H NMR (400 MHz, DMSO-d₆, TFA-d₁) δ [ppm] 7.98-7.94 (m, 2H), 7.79-7.74 (m, 2H), 7.70-7.62 (m, 4H), 6.99 (d, J=2.1 Hz, 1H), 3.91-3.20 (m, 8H), 3.11-2.84 (m, 2H), 2.36-2.21 (m, 2H), 1.10-0.99 (m, 3H);

1-[5-(4-isoquinolin-6-yl-benzoyl)-hexahydro-pyrrolo[3,4-c]pyrrol-2-yl]-ethanone ("A3")

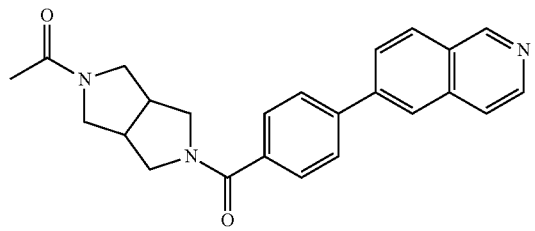 [SMILES: CC(=O)N1CC2CN(C(=O)c3ccc(-c4ccc5cnccc5c4)cc3)CC2C1]

¹H NMR (400 MHz, DMSO-d₆, TFA-d₁) δ [ppm] 9.96 (s, 1H), 8.75-8.66 (m, 3H), 8.57 (d, J=6.7 Hz, 1H), 8.43 (dd, J=8.7, 1.6 Hz, 1H), 8.04 (d, J=8.3 Hz, 2H), 7.78 (d, J=8.4 Hz, 2H), 3.92-3.22 (m, 8H), 3.14-2.87 (m, 2H), 2.02 (d, J=13.3 Hz, 3H);

1-{5-[4-(1H-indol-6-yl)-benzoyl]-hexahydro-pyrrolo[3,4-c]pyrrol-2-yl}-propan-1-one ("A4")

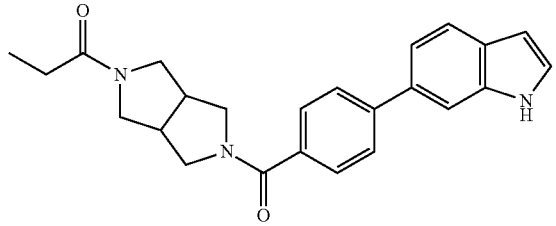 [SMILES: CCC(=O)N1CC2CN(C(=O)c3ccc(-c4ccc5cc[nH]c5c4)cc3)CC2C1]

¹H NMR (400 MHz, DMSO-d₆,) δ [ppm] 7.75-7.70 (m, 2H), 7.67 (d, J=0.7 Hz, 1H), 7.65-7.58 (m, 3H), 7.45-7.37 (m, 1H), 7.34 (dd, J=8.3, 1.6 Hz, 1H), 6.47-6.44 (m, 1H), 3.82-3.08 (m, 8H) 3.05-2.78 (m, 2H), 2.31-2.16 (m, 2H), 1.04-0.94 (m, 3H);

(5-cyclopropanecarbonyl-hexahydro-pyrrolo[3,4-c]pyrrol-2-yl)-[4-(1H-indol-6-yl)-phenyl]-methanone ("A5")

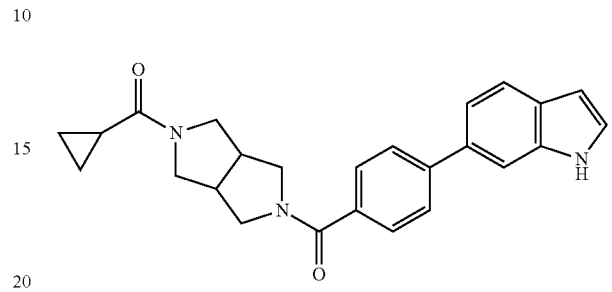

¹H NMR (400 MHz, DMSO-d₆,) δ [ppm] 11.19 (s, 1H), 7.73 (d, J=8.4 Hz, 2H), 7.68 (s, 1H), 7.62 (t, J=7.5 Hz, 3H), 7.43-7.37 (m, 1H), 7.34 (dd, J=8.3, 1.6 Hz, 1H), 6.48-6.43 (m, 1H), 3.92-3.12 (m, 8H), 3.10-2.80 (m, 2H), 1.85-164 (m, 1H), 0.81-0.66 (m, 4H);

1-[5-(4-benzofuran-6-yl-benzoyl)-hexahydro-pyrrolo[3,4-c]pyrrol-2-yl]-ethanone ("A6")

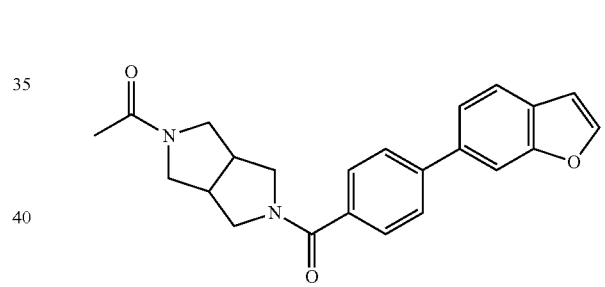

¹H NMR (400 MHz, DMSO-d₆,) δ [ppm] 7.97 (s, 2H), 7.80-7,74 (m, 2H), 7.72-7.63 (m, 4H), 7.02-6.97 (m, 1H), 3.90-3.20 (m, 8H), 3.13-2.86 (m, 2H), 2.07-1.97 (m, 3H);

1-{5-[4-(1H-indol-6-yl)-benzoyl]-hexahydro-pyrrolo[3,4-c]pyrrol-2-yl}-ethanone ("A7")

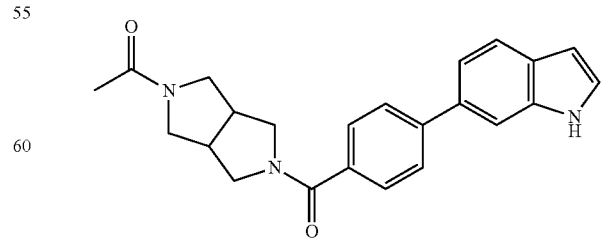

¹H NMR (400 MHz, DMSO-d₆, TFA-d₁) δ [ppm] 7.76-7,66 (m, 3H), 7.65-7.58 (m, 3H), 7.43-7.38 (m, 1H), 7.34 (dd, J=8.3, 1.6 Hz, 1H), 6.49-6.42 (m, 1H), 3.82-3.10 (m 8H), 2.93 (d, J=40.2 Hz, 2H), 1.94 (d, J=9.9 Hz, 3H);

(5-cyclopropanecarbonyl-hexahydro-pyrrolo[3,4-c]pyrrol-2-yl)-(4-isoquinolin-6-yl-phenyl)-methanone ("A8")

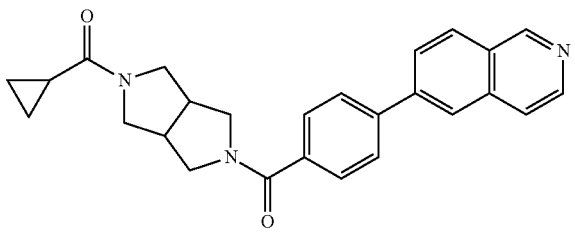 [SMILES: O=C(c1ccc(-c2ccc3cnccc3c2)cc1)N1CC2CN(C(=O)C3CC3)CC2C1]

$^1$H NMR (500 MHz, DMSO-d$_6$,) δ [ppm] 8.75-8.64 (m, 3H), 8.57 (d, J=6.6 Hz, 1H), 8.43 (d, J=8.8 Hz, 1H), 8.04 (d, J=8.2 Hz, 2H), 7.79 (d, J=8.1 Hz, 2H), 4.11-3.63 (m, 4H), 3.65-3.18 (m, 5H), 3.02 (dd, J=63.6, 19.4 Hz, 2H), 1.75 (d, J=27.8 Hz, 1H), 0.90-0.65 (m, 4H);

(4-benzofuran-6-yl-phenyl)-(5-cyclopropanecarbonyl-hexahydro-pyrrolo[3,4-c]pyrrol-2-yl)-methanone ("A9")

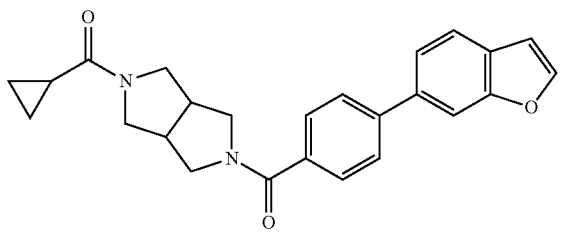 [SMILES: O=C(c1ccc(-c2ccc3ccoc3c2)cc1)N1CC2CN(C(=O)C3CC3)CC2C1]

$^1$H NMR (500 MHz, DMSO-d$_6$,) δ [ppm] 8.04 (d, J=2.2 Hz, 1H), 7.97 (d, J=1.7 Hz, 1H), 7.75 (d, J=8.3 Hz, 2H), 7.70 (d, J=8.6 Hz, 1H), 7.66-7.59 (m, 3H), 7.02 (dd, J=2.1, 0.8 Hz, 1H), 3.98-3.58 (m, 4H), 3.55-3.36 (m, 3H), 3.23-3.13 (m, 1H), 3.11-2.79 (m, 2H), 1.81-1.66 (m, 1H), 0.80-0.65 (m, 4H).

Pharmacological Data

TABLE 2

Inhibition of FASN of some representative compounds of the formula I

| Compound No. | IC$_{50}$ FASN (enzyme assay) |
|---|---|
| "A1" | A |
| "A2" | B |
| "A3" | B |
| "A4" | B |
| "A5" | B |
| "A6" | C |
| "A7" | B |
| "A8" | B |
| "A9" | |

IC$_{50}$: <0.3 μM = A 0.3-3 μM = B 3-50 μM = C

The compounds shown in Table 2 are particularly preferred compounds according to the invention.

The following examples relate to medicaments:

EXAMPLE A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient of the formula I, 9.38 g of NaH$_2$PO$_4$.2 H$_2$O, 28.48 g of Na$_2$HPO$_4$.12 H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:

1. A compound of formula I

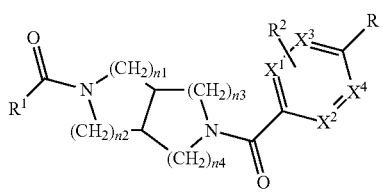

wherein
R$^1$ denotes A or Cyc,
R$^2$ denotes H,
R denotes Het,
X$^1$, X$^2$, X$^3$, X$^4$ each, independently of one another, denote CH or N,
A denotes unbranched or branched alkyl with 1-6 C-atoms, wherein 1-5 H-atoms are each optionally replaced by F,
Cyc denotes cycloalkyl with 3-7 C-atoms,
Het denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzoxazolyl, benzothiazolyl, benzimidazolyl, benzotriazolyl, indolyl, benzo-1,3-dioxolyl, benzodioxanyl, benzothiadiazolyl, indazolyl, benzofuranyl, quinolyl or isoquinolyl, which is unsubstituted or mono-or disubstituted by Hal or A,
Hal denotes F, Cl, Br or I,
n1, n2, n3, n4 each denote 1,
with the proviso that only one or two of X$^1$, X$^2$, X$^3$, X$^4$ may denote N, or
a pharmaceutically acceptable salt, tautomers or stereoisomer thereof, including mixtures thereof.

2. A compounds according to claim 1, wherein said compound is selected from:

| No. | Name |
|---|---|
| "A1" | 1-[5-(4-isoquinolin-6-yl-benzoyl)-hexahydro-pyrrolo[3,4-c]pyrrol-2-yl]-propan-1-one |
| "A2" | 1-[5-(4-benzofuran-6-yl-benzoyl)-hexahydro-pyrrolo[3,4-c]pyrrol-2-yl]-propan-1-one |
| "A3" | 1-[5-(4-isoquinolin-6-yl-benzoyl)-hexahydro-pyrrolo[3,4-c]pyrrol-2-yl]-ethanone |
| "A4" | 1-{5-[4-(1H-indol-6-yl)-benzoyl]-hexahydro-pyrrolo[3,4-c]pyrrol-2-yl}-propan-1-one |
| "A5" | (5-cyclopropanecarbonyl-hexahydro-pyrrolo[3,4-c]pyrrol-2-yl)-[4-(1H-indol-6-yl)-phenyl]-methanone |
| "A6" | 1-[5-(4-benzofuran-6-yl-benzoyl)-hexahydro-pyrrolo[3,4-c]pyrrol-2-yl]-ethanone |
| "A7" | 1-{5-[4-(1H-indol-6-yl)-benzoyl]-hexahydro-pyrrolo[3,4-c]pyrrol-2-yl}-ethanone |
| "A8" | (5-cyclopropanecarbonyl-hexahydro-pyrrolo[3,4-c]pyrrol-2-yl)-(4-isoquinolin-6-yl-phenyl)-methanone |
| "A9" | (4-benzofuran-6-yl-phenyl)-(5-cyclopropanecarbonyl-hexahydro-pyrrolo[3,4-c]pyrrol-2-yl)-methanone | and
pharmaceutically acceptable salts, tautomers and stereoisomers thereof, including mixtures thereof.

3. A compound according to claim 1, in which
X$^1$ and X$^3$ each denote CH, and
X$^2$ and X$^4$ each denote N.

4. A compound according to claim 1, in which
X$^1$, X$^2$, X$^3$, and X$^4$ each denote CH.

5. A compound according to claim 1, in which
X$^1$ X$^3$, and X$^4$ each denote CH, and
X$^2$ denotes N.

6. A compound according to claim 1, in which
X$^1$ X$^2$, and X$^3$ each denote CH, and
X$^4$ denotes N.

7. A compound according to claim 1, in which
X$^1$ and X$^2$ each denote CH, and
X$^3$ and X$^4$ each denote N.

8. A compound according to claim 1, in which
X$^3$ and X$^4$ each denote CH, and
X$^1$ and X$^2$ each denote N.

9. A compound according to claim 4, in which Het is indolyl benzofuranyl, or isoquinolyl, which is unsubstituted or mono-or disubstituted by Hal or A.

10. A compound according to claim 2, wherein said compound is 1-[5-(4-isoquinolin-6-yl-benzoyl)-hexahydro-pyrrolo[3,4-c]pyrrol-2-yl]-propan-1-one or a pharmaceutically acceptable salt, tautomer or stereoisomer thereof, including mixtures thereof.

11. A compound according to claim 2, wherein said compound is 1-[5-(4-benzofuran-6-yl-benzoyl)-hexahydro-pyrrolo[3,4-c]pyrrol-2-yl]-propan-1-one or a pharmaceutically acceptable salt, tautomer or stereoisomer thereof, including mixtures thereof.

12. A compound according to claim 2, wherein said compound is 1-[5-(4-isoquinolin-6-yl-benzoyl)-hexahydro-pyrrolo[3,4-c]pyrrol-2-yl]-ethanone or a pharmaceutically acceptable salt, tautomer or stereoisomer thereof, including mixtures thereof.

13. A compound according to claim 2, wherein said compound is 1-{5-[4-(1H-indo-6-yl)-benzoyl]-hexahydro-pyrrolo[3,4-c]pyrrol-2-yl}-propan-1-one or a pharmaceutically acceptable salt, tautomer or stereoisomer thereof, including mixtures thereof.

14. A compound according to claim 2, wherein said compound is (5-cyclopropanecarbonyl-hexahydro-pyrrolo[3,4-c]pyrrol-2-yl)-[4-(1H-indol-6-yl)-phenyl]-methanone or a pharmaceutically acceptable salt, tautomer or stereoisomer thereof, including mixtures thereof.

15. A compound according to claim 2, wherein said compound 1-{5-[4- (1H-indol-6-yl)-benzoyl]-hexahydro-pyrrolo [3,4-c]pyrrol-2-yl}-ethanone or a pharmaceutically acceptable salt, tautomer or stereoisomer thereof, including mixtures thereof.

16. A compound according to claim 2, wherein said compound 1(5-cyclopropanecarbonyl-hexahydro-pyrrolo [3,4-c] pyrrol-2-yl)-(4-isoquinolin-6-yl-phenyl)-methanone or a pharmaceutically acceptable salt, tautomer or stereoisomer thereof, including mixtures thereof.

17. A process for the preparation of a according to claim 1, said process comprising:
reacting a compound of formula II

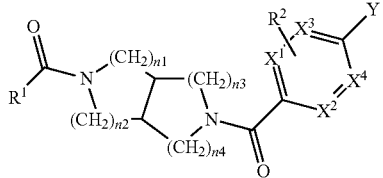

II in which $R^1, R^2, X^1, X^2, X^3, X^4$ n1, n2, n3 and n4 have the meanings indicated in claim 1, and
Y denotes Br or I,
with a compound of formula III

R-L                          III in which R has the meaning indicated in claim 1,
and L denotes a boronic acid or a boronic acid ester group,
in a Suzuki-type coupling, and/or
converting a base or acid of formula I into one of its salts.

18. A composition comprising at least one compound according to claim 1, and a pharmaceutically acceptable carrier, excipient or vehicle.

19. A composition comprising at least one compound according to claim 1, a pharmaceutically acceptable carrier, excipient or vehicle, and at least one further medicament active ingredient selected from anticancer agents.

20. A kit comprising separate packs of
(a) an effective amount of a compound according to claim 1, and
(b) an effective amount of a further medicament active ingredient selected from anticancer agents.

* * * * *